United States Patent [19]

Dumont et al.

[11] 4,196,209

[45] Apr. 1, 1980

[54] TREATING PSYCHIC DISORDERS WITH PIPERIDYL-INDOLES

[75] Inventors: Claude Dumont, Nogent-sur-Marne; Jacques Guillaume, Sevran; Lucien Nedelec, Le Raincy, all of France

[73] Assignee: Roussel Uclaf, Paris, France

[21] Appl. No.: 820,835

[22] Filed: Aug. 1, 1977

[30] Foreign Application Priority Data

Aug. 26, 1976 [FR] France .................................. 76 25798

[51] Int. Cl.² .................. A61K 31/445; A61K 31/44; C07D 401/04
[52] U.S. Cl. .................................. 424/267; 424/263; 546/201; 546/273
[58] Field of Search .................. 260/293.61, 296 B; 424/263, 267; 546/201, 273

[56] References Cited

U.S. PATENT DOCUMENTS

| | | | |
|---|---|---|---|
| 2,872,453 | 2/1959 | Jacob et al. | 546/273 |
| 3,361,759 | 1/1968 | Anthony et al. | 260/293.61 |
| 3,850,938 | 11/1974 | Derible et al. | 260/293.61 |
| 3,980,658 | 9/1976 | Possanza et al. | 260/293.61 |
| 3,993,764 | 11/1976 | Dumont et al. | 424/267 |
| 4,100,291 | 7/1978 | Clemence et al. | 546/273 |

OTHER PUBLICATIONS

Boissier, J. et al., *Therapie*, 18, 1257-1277 (1963).

Ungerstedt, *Acta Physiol. Scand.*, 82, Supp. 367, pp. 69-93 (1971).
Malatray, J. et al., *J. Pharmacol.* (Paris), 1972, 3(3), 325-342.
Bergman, J., *J. Heterocyclic Chem.*, 7, 1071-1076 (1970).

*Primary Examiner*—John M. Ford
*Assistant Examiner*—Richard A. Schwartz
*Attorney, Agent, or Firm*—Hammond & Littell, Weissenberger and Muserlian

[57] ABSTRACT

Novel piperidyl-indoles of the formula

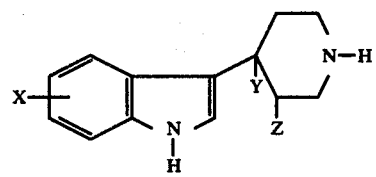

I wherein X is selected from the group consisting of fluorine, chlorine and bromine when Y and Z are hydrogen or together form a double bond and X is selected from the group consisting of hydrogen and alkoxy of 1 to 3 carbon atoms when Y and Z form a double bond and their non-toxic, pharmaceutically acceptable acid addition salts having antidepressant, antiemetic and antiparkinsonian activity and their preparations and novel intermediates therefore.

16 Claims, No Drawings

TREATING PSYCHIC DISORDERS WITH PIPERIDYL-INDOLES

STATE OF THE ART

French Pat. No. 2,227,873 and U.S. Pat. No. 3,993,764 describe different piperidyl-indoles.

OBJECTS OF THE INVENTION

It is an object of the invention to provide the novel piperidyl-indoles of formula I and their non-toxic, pharmaceutically acceptable acid addition salts and to a novel process for their preparation and to novel intermediates formed therein.

It is another object of the invention to provide novel compositions for treating psychic troubles and to a novel method of treating psychic troubles in warm-blooded animals.

These and other objects and advantages of the invention will become obvious from the following detailed description.

THE INVENTION

The novel piperidyl-indoles of the invention are selected from the group consisting of compounds of the formula

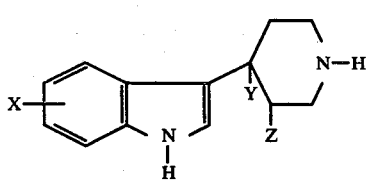

wherein X is selected from the group consisting of fluorine, chlorine and bromine and Y and Z are hydrogen or together form a double bond and X is selected from the group consisting of hydrogen and alkoxy of 1 to 3 carbon atoms when Y and Z form a double bond and their non-toxic, pharmaceutically acceptable acid addition salts.

Preferably the X substituent is in the 4,5 or 6-position of the indole nucleus and examples of suitable alkoxy groups of 1 to 3 carbon atoms are methoxy, ethoxy and propoxy.

Examples of suitable acids for the formation of the non-toxic, pharmaceutically acceptable acid addition salts are mineral acids such as hydrochloric acid, hydrobromic acid, hydroiodic acid, nitric acid, sulfuric acid or phosphoric acid and organic acids such as acetic acid, formic acid, benzoic acid, maleic acid, fumaric acid, succinic acid, tartaric acid, citric acid, oxalic acid, glyoxylic acid, aspartic acic, alkanesulfonic acids such as methane sulfonic acid and aryl sulfonic acids such as benzene sulfonic acid.

Among the preferred compounds of formula I are those where X is chlorine and Y and Z form a double bond or are hydrogen and those wherein X is hydrogen or methoxy and Y and Z form a double bond and their non-toxic, pharmaceutically acceptable acid addition salts. Most preferred is the former group.

The novel process of the invention for the preparation of the compounds of formula I wherein X is fluorine, chlorine or bromine and Y and Z are hydrogen comprises reacting a compound of the formula

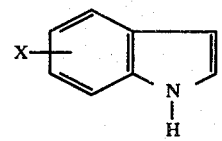

wherein X is fluorine, chlorine or bromine with acetyl chloride and pyridine to obtain a compound of the formula

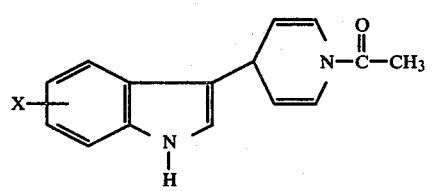

reducing the latter to obtain a compound of the formula

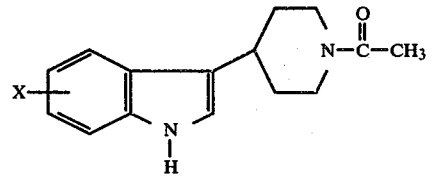

and saponifying the latter to obtain the corresponding compound of claim 1 wherein Y and Z are hydrogen and X is fluorine, chlorine or bromine which may be treated with an acid, if desired, to form the corresponding acid addition salts.

In a preferred mode of the process, the reduction of the compound of formula III is effected with hydrogen in the presence of a catalyst such as platinum oxide or palladium hydroxide and the saponification is effected with potassium hydroxide in a refluxing lower alkanol such as propanol.

The process of the invention to prepare the compounds of formula I wherein X is hydrogen or alkoxy of 1 to 3 carbon atoms or chlorine, fluorine or bromine and Y and Z form a double bond comprises reacting a compound of the formula

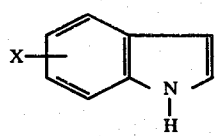

wherein X is hydrogen, bromine, chlorine, fluorine or alkoxy of 1 to 3 carbon atoms with 4-piperidone hydrochloride in acetic acid in the optional presence of a strong acid to obtain an acid salt of a compound of the formula

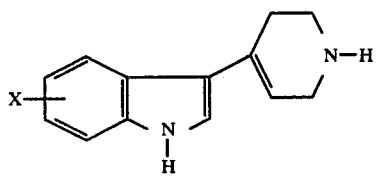

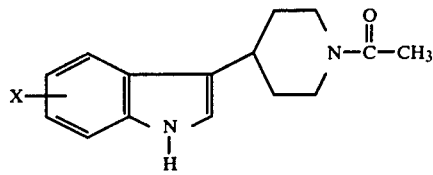

which may be treated with a base to form the corresponding free base which may be salified if desired. Preferably, the strong acid is phosphoric acid and the reaction is effected between room temperature and the reflux temperature.

The compounds of formula I are basic is nature and can therefore be salified by reaction with a substantially stoichiometric amount of an acid.

The novel compositions of the invention having anti-depressive, antiemetic and antiparkinsonian activity are comprised of an effective amount of at least one compound of formula I and is non-toxic, pharmaceutically acceptable acid addition salts and an inert pharmaceutical carrier. The compositions may be in the form of tablets, dragees, gelules, granules, capsules, suppositories or injectable solutions or suspensions.

Examples of suitable carriers or excipients are talc, arabic gum, lactose, starch, magnesium stearate, cacao butter, aqueous or non-aqueous vehicles, fatty bodies of animal or vegetable origin, paraffinic derivatives, glycols, preservatives, diverse wetting agents, dispersants and emulsifiers.

The compositions are useful for the treatment of psychic troubles, behavoir problems, character problems, in the treatment of akinetic and dyskinetic states as well as treatment of vomitting and nausea of all origins.

Particularly preferred are the compositions containing compounds of formula I where X is chlorine and Y and Z form a double bond or are hydrogen and those wherein X is hydrogen or methoxy and Y and Z form a double bond and their non-toxic, pharmaceutically acceptable acid addition salts. Most preferred is the former group.

The novel method of the invention for the treatment of psychic disorders in warm-blooded animals, including humans, comprises administering to warm-blooded animals an amount of at least one compound of formula I and its non-toxic, pharmaceutically acceptable acid addition salts to relieve psychic disorders. The compounds may be administered orally, rectally or parenterally, preferably orally. The usual useful dose is 0.1 to 10 mg/kg when adminstered orally.

The novel intermediate compounds of the invention have the formulae

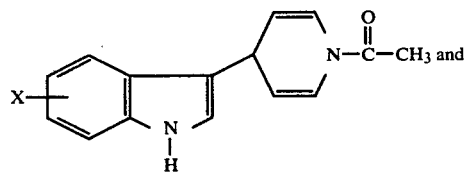

wherein X is fluorine, chlorine or bromine.

In the following examples there are described several preferred embodiments to illustrate the invention. However, it should be understood that the invention is not intended to be limited to the specific embodiments.

EXAMPLE 1

5-chloro-3-(4-piperidyl)-1H-indole hydrochloride

STEP A: 3-(1-acetyl-1,4-dihydro-4-pyridyl)-5-chloro-1H-indole 27 ml of redistilled pyridine were added at an interior temperature of 8° to 15° C. to a mixture of 11.2 ml of acetyl chloride and 120 ml of dioxane cooled in an ice bath and a mixture of 22 g of 5-chloro-1H-indole in 120 ml of dioxane was added to the resulting suspension at 10° to 15° C. The mixture was stirred in the dark at room temperature for 7 hours and the suspension was poured into 500 ml of water. The mixture was stirred for 5 minutes and another 500 ml of water were added. The mixture was filtered and the recovered solid was empasted with 40 ml of acetonitrile, was filtered, rinsed with acetonitrile and once with ether to obtain 13.5 g of 3-(1-acetyl-1,4-dihydro-4-pyridyl)-5-chloro-1H-indole in the form of a pale yellow solid melting at 202° C.

Analysis: $C_{15}H_{13}ClN_2O$; molecular weight=272.747. Calculated: %C 66.06; %H 4.80; %Cl 13.0; %N 10.27. Found: 66.0; 4.9; 13.1; 10.4.

STEP B: 3-(1-acetyl-4-piperidyl)-5-chloro-1H-indole

Hydrogen was absorbed into a mixture of 8.49 g of the product of Step A, 850 mg of platinum oxide and 420 ml of ethanol until saturation was reached and the mixture was filtered. The filter was rinsed with ethanol and the filtrate was evaporated to dryness to obtain 9 g of raw product. The latter was taken up in 10 ml of acetonitrile and the mixture was stirred at room temperature for 20 minutes and was filtered. The filter was rinsed with acetonitrile to obtain 6.99 g of product which was crystallized from hot and cold ethanol and dried to obtain 4.78 g of 3(1-acetyl-4-piperidyl)-5-chloro-1H-indole in the form of a colorless solid melting at 201° C.

Analysis: $C_{15}H_{17}ClN_2O$; molecular weight=276.779. Calculated: %C 65.1; %G 6.19; %Cl 12.81; %N 10.12. Found: 65.2; 6.3; 12.6; 10.1.

STEP C: 5-chloro-3-(4-piperidyl)-1H-indolehydrochloride

A mixture of 6.02 g of the product of Step B, 6 g of potassium hydroxide and 50 ml of propanol was refluxed for 4 hours and was then cooled and poured into 500 ml of ice water. The mixture was stirred for 45 minutes at room temperature and was then filtered. The recovered product was rinsed with water and dried at 50° C. under reduced pressure to obtain 5.02 g of 5-chloro-3-(4-piperidyl)-1H-indole melting at 208° C.

5.5 g of the said product were suspended in 120 ml of ethyl acetate and 10 ml of ethyl acetate saturated with hydrogen chloride were added thereto with stirring and cooling. The mixture was stirred on an ice bath for 15 minutes and was then filtered. The product was rinsed with ethyl acetate and then with ether to obtain 5.89 g of raw product which was crystallized from hot and cold ethanol. The product was rinsed with ethanol, then ether and dried at room temperature under reduced pressure to obtain 2.86 g of 5-chloro-3-(4-piperidyl)-1H-indole hydrochloride in the form of a colorless solid melting at 260°–262° C.

Analysis: $C_{13}H_{15}Cl_2N_2$; molecular weight=271.198. Calculated: %C 57.57; %H 5.95; %Cl 26.15; %N 10.33. Found: 57.3; 6.0; 25.8; 10.2.

EXAMPLE 2

Neutral succinate of 3-(1,2,3,6-tetrahydro-4-pyridyl)-1H-indole 50 ml of aqueous N phosphoric acid and 39.3 g of the hydrochloride of 4-piperidone monohydrate were added under nitrogen with stirring to a solution of 10 g of indole in 200 ml of acetic acid at 95°–100° C. and the mixture was heated at 100° C. for an hour and was then cooled. The mixture was poured into ice containing 350 ml of concentrated ammonium hydroxide and the mixture was extracted with ethyl acetate. The organic extracts were washed with water, aqueous sodium chloride, dried over magnesium sulfate and evaporated to dryness to obtain 14.7 g of raw product. The latter was empasted with 75 ml of methanol under nitrogen and was vacuum filtered. The recovered precipitate was rinsed with methanol and ether to obtain 1.42 g of 3-(1,2,3,6-tetrahydro-4-pyridyl)-1-H-indole melting at 185°–186° C. The mother liquor was evaporated to dryness and the raw product was chromatographed over silica gel. Elution with a 6-3-1 chloroform-methanol-triethylamine mixture yielded 4.55 g of product with an Rf=0.15. The latter was empasted with ether to obtain 4.295 g of 3-(1,2,3,6-tetrahydro-4-pyridyl)-1H-indole for a total yield of 5.715 g of product. The latter was crystallized from hot and cold isopropanol to obtain 3.56 g of 3-(1,2,3,6-tetrahydro-4-pyridyl)-1H-indole melting at 190°–191° C.

2.26 g of succinic acid were added to a solution of 3.8 g of the above product in 200 ml of methanol and the resulting precipitated product was dissolved in refluxing methanol. The mixture was filtered hot and was concentrated to induce crystallization. The product was purified a second time by the same procedure to obtain 2.65 g of neutral succinate of 3-(1,2,3,6-tetrahydro-4-pyridyl)-1H-indole melting at 238°–240° C.

Analysis: $C_{30}H_{34}N_4O_4$; molecular weight=514.60. Calculated: %C 70.02; %H 6.66; %N 10.89. Found: 69.7; 6.6; 10.9.

EXAMPLE 3

Neutral succinate of 5-methoxy-3-(1,2,3,6-tetrahydro-4-pyridyl)-1H-indole 44 g of the hydrochloride of 4-piperidone monohydrate were added at 100° C. to a solution of 12.6 g of 5-methoxy-1H-indole in 240 ml of acetic acid and the mixture was held at 100° C. for 30 minutes and was then cooled. The mixture was poured into ice water containing 400 ml of concentrated ammonium hydroxide and was extracted with ethyl acetate. The organic phase was washed with aqueous sodium chloride solution, dried over magnesium sulfate and evaporated to dryness to obtain 20 g of raw product. The latter was chromatographed over silica gel and was eluted with a 7-2-1 chloroform-methanol-triethylamine mixture to obtain 5.26 g of 5-methoxy-3-(1,2,3,6-tetrahydro-4-pyridyl)-1H-indole in the form of a resin.

The latter product was dissolved in 100 ml of methanol and a solution of 1.22 g of succinic acid in 10 ml of methanol was added thereto. Crystallization was induced and the mixture was filtered. The recovered product was rinsed with methanol and then with ethanol to obtain 4.4 g of the neutral succinate of 5-methoxy-(1,2,3,6-tetrahydro-4-pyridyl)-1H-indole in the form of crystals melting of 255°–258° C.

Analysis: $C_{32}H_{38}N_4O_6$: molecular weight=574.683. Calculated: %C 66.88; %H 6.66; %N 9.74. Found: 66.6; 6.8; 9.6.

EXAMPLE 4

Neutral succinate of 5-chloro-3-(1,2,3,6-tetrahydro-4-pyridyl)-1H-indole 47.5 g of the hydrochloride of 4-piperidone monohydrate were added to a solution of 9.05 g of 5-chloro-1H-indole in 180 ml of acetic acid at 90° C. and the mixture was held at 90°–100° C. for one hour and was then cooled. The mixture was poured into ice water containing 300 ml of concentrated ammonium hydroxide and the mixture was extracted with ethyl acetate. The organic extracts were washed with water and aqueous sodium chloride solution, were dried over magnesium sulfate and were evaporated to dryness to obtain 12.816 g of raw product. The latter was taken up in a 6-3-1 chloroform-methanol-triethylamine mixture and the mixture was vacuum filtered. The filtrate was chromatographed over silica gel and was eluted with a 6-3-1 chloroform-methanol-triethylamine mixture to obtain after evaporation 5.973 g of 5-chloro-3-(1,2,3,6-tetrahydro-4-pyridyl)-1H-indole in the form of a yellow resin.

The latter was dissolved in 50 ml of methanol and 3g of succinic acid were added thereto. Crystallization was started and the mixture was iced for 30 minutes and was then vacuum filtered. The recovered precipitate was rinsed with methanol and was dried to obtain 5.466 g of the neutral succinate of 5-chloro-3-(1,2,3,6-tetrahydro-4-pyridyl)-1H-indole in the form of yellow crystals melting at 253°–254° C.

Analysis: $C_{30}H_{32}Cl_2N_4O_4$; molecular weight=583.52. Calculated: %C 61.75; %H 5.52; %Cl 12.15; %N 9.60. Found: 61.5; 5.6; 12.2; 9.4.

EXAMPLE 5

Neutral succinate of 4-methoxy-3-(1,2,3,6-tetrahydro-4-pyridyl)-1H-indole

Using the procedure of Example 3, 4-methoxy-1H-indole was reacted to obtain the neutral succinate of 4-methoxy-3-(1,2,3,6-tetrahydro-4-pyridyl)-1H-indole in the form of crystals melting at 160° C. and then 194°–196° C.

EXAMPLE 6

Tablets were prepared containing 25 mg of 5-chloro-3-(4-piperidyl)-1H-indole hydrocloride and sufficient excipient to obtain a final tablet of 200 mg. An injectable solution was prepared with 25 mg of the neutral succinate of 5-methoxy-3-(1,2,3,6-tetrahydro-4-pyridyl)-1H-indole and sterile aqueous excipient to obtain 2 ml of solution.

PHARMACOLOGICAL DATA

A. Potentialization of amphetamine stereotypies

The tests were effected on groups of 5 male rats weighing 150 to 180 g with the animals individually placed in a grilled cage (29×25×17 cm) containing a few scraps of wood chips. A delay of one hour was observed between the intraperitoneal administration of the test compound and the intraperitoneal injection of 5 mg/kg of dexamphetamine sulfate and the behavoir of the animals was noted every half hour for 5 hours with the preconceived readings of Halliwell et al [Brit. J. Pharmacol., Vol. 23 (1964), p. 330–350] as follows: The animal was asleep (0), the animal was awake but immobile (1), the animal was turning in the cage (2), the animal was sniffing the cover (3), the animal was licking the sides (4), the animal was touching the cover or bars of the cage with his teeth (5), and the animal was gnawing on the bars or cover of the cage (6).

The intensity of the stereotypies were expressed in a form of a score of 0 to 30 corresponding to the total of the values obtained for each group of 5 rats. The sum of the scores totaled in 5 hours was calculated. The dose of the test compound which augmented by about 100% the sum of the scores in 5 hours was 10 mg/kg for the product of Examples 1 and 2 and 3 mg/kg for the product of Example 3.

B. Antagonism towards catalepsy caused by prochlororpemazine

The test was effected on groups of 5 male rats weighing about 100 g and the test compound was administered intraperitoneally simultaneously with the intraperitoneal administration of 15 mg/kg of prochloropemazine. The catalepsy was observed every hour for 7 hours following the test of crossing of homolateral paws [Boissier et al., Therapie, Vol. 18 (1963), p. 1257–1277] with the following notations: The animal refused to cross the front paws with the homolateral rear paws (0); the animals accepted the crossing only for one side (0.5) and the animal accepted the crossing of both sides (1). The compounds of Examples 1 and 3 opposed catalepsy induced by prochlorpemazine at a dose below 20 mg/kg while the compound of Example 2 was effective at a dose below 10 mg/kg.

C. Antiemetic Activity

The antagonism to vomitting provoked by apomorphine was studied in dogs [Chen et al., J. Pharmac. exp. Therap., Vol. 93 (1959), p. 245–250] and the number of vomits provoked by subcutaneous injection of 0.1 mg/kg of apomorphine hydrochloride was determined for each animal 8 days before the test. The test compound in aqueous solution was subcutaneously administered at varying doses one half hour before the apomorphine hydrochloride. The compound of Example 1 was antagonistic to the provoked vomits at 2 mg/kg, the compound of Example 2 was effective at 5 mg/kg and the compound of Example 3 was effective at less than 1 mg/kg.

D. Acute Toxicity

The acute toxicity was determined on groups of 10 mice weighing about 20 g and the test compounds were intraperitoneally administered at increasing doses. The mortality was determined 48 hours after the administration and the $LD_{50}$ dose for the compounds of Examples 1 and 2 was 150 mg/kg and was 120 mg/kg for the compound of Example 3.

Various modifications of the products and processes of the invention may be made without departing from the spirit or scope thereof and it is to be understood that the invention is intended to be limited only as defined in the appended claims.

We claim:

1. A compound selected from the group consisting of compounds of the formula

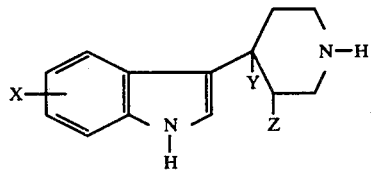

wherein X is selected from the group consisting of fluorine, chlorine and bromine when Y and Z are hydrogen or together form a double bond and X is selected from the group consisting of hydrogen and alkoxy of 1 to 3 carbon atoms when Y and Z form a double bond and their non-toxic, pharmaceutically acceptable acid addition salts.

2. A compound of claim 1 wherein X is chlorine and Y and Z are hydrogen or together form a double bond.

3. A compound of claim 1 wherein Y and Z together form a double bond and X is hydrogen or methoxy.

4. A compound of claim 1 which is 5-chloro-3-(4-piperidyl)-1H-indole hydrochloride.

5. A compound of claim 1 which is the neutral succinate of 3-(1,2,3,6-tetrahydro-4-pyridyl)-1H-indole.

6. A compound of claim 1 which is the neutral succinate of 5-methoxy-3-(1,2,3,6-tetrahydro-4-pyridyl)-1H-indole.

7. A compound of claim 1 which is the neutral succinate of 4-methoxy-3-(1,2,3,6-tetrahydro-4-pyridyl)-1H-indole 8. A composition for treating psychic disorders comprising an amount effective to combat psychic disorders of at least one compound of claim 1 and an inert pharmaceutical carrier.

9. A composition of claim 8 wherein X is chlorine and Y and Z are hydrogen or together form a double bond.

10. A composition of claim 8 wherein Y and Z together form a double bond and X is hydrogen or methoxy.

11. A method of treating psychic disorders in warmblooded animals comprising administering to warmblooded aniamls an amount of at least one compound of claim 1 sufficient to relieve psychic disorders.

12. The method of claim 11 wherein X is chlorine and Y and Z are hydrogen or together form a double bond.

13. The method of claim 11 wherein Y and Z together form a double bond and X is hydrogen or methoxy.

14. The method of claim 11 wherein the compound is 5-chloro-3-(4-piperidyl)-1H-indole hydrochloride.

15. The method of claim 11 wherein the compound is the neutral succinate of 3-(1,2,3,6-tetrahydro-4-pyridyl)-1H-indole.

16. The method of claim 11 wherein the compound in the neutral succinate of 4-methoxy-3-(1,2,3,6-tetrahydro-4-pyridyl)-1H-indole.

* * * * *